Figure 1:
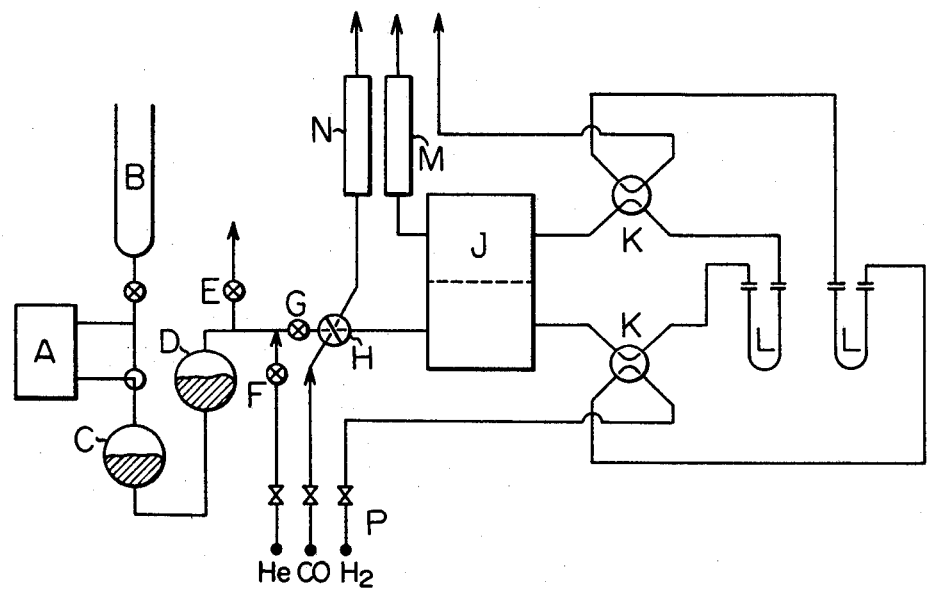

United States Patent [19]

Matsunaga et al.

[11] 4,322,567
[45] Mar. 30, 1982

[54] PROCESS FOR PRODUCTION OF AROMATIC ALCOHOLS

[75] Inventors: Fujihisa Matsunaga, Iwakuni; Norio Ohno, Yamaguchi; Hirohiko Nambu, Iwakuni, all of Japan

[73] Assignee: Mitsui Petrochemical Industries Ltd., Tokyo, Japan

[21] Appl. No.: 152,155

[22] Filed: May 22, 1980

[30] Foreign Application Priority Data

Jun. 18, 1979 [JP] Japan .................................. 74-75624

[51] Int. Cl.³ ...................... C07C 27/04; C07C 27/06
[52] U.S. Cl. ................................... 568/815; 568/807; 568/819; 568/814; 568/798
[58] Field of Search ............... 568/815, 819, 798, 741, 568/768, 807, 814

[56] References Cited

FOREIGN PATENT DOCUMENTS 39-26961 11/1964 Japan .................................. 568/815
50-4036 1/1975 Japan .................................. 568/815
792558 3/1958 United Kingdom ............... 568/815

Primary Examiner—Werren B. Lone
Attorney, Agent, or Firm—Sherman & Shalloway

[57] ABSTRACT

In a process for producing an aromatic alcohol by catalytic hydrogenation of at least one tertiary peroxide selected from the group consisting of tertiary aromatic hydroperoxides and tertiary aromatic peroxides in the presence of a palladium catalyst in a lower aliphatic alcohol solvent to form the corresponding alcohol; the improvement wherein said catalyst has a palladium metal surface area, determined by the CO chemisorption method, of up to about 200 m²/g·Pd.

3 Claims, 1 Drawing Figure

PROCESS FOR PRODUCTION OF AROMATIC ALCOHOLS

This invention relates to an improved process which can advantageously avoid technical troubles associated with the production of an aromatic alcohol by the catalytic hydrogenation of a tertiary peroxide selected from the group consisting of tertiary aromatic hydroperoxides, tertiary aromatic peroxides and the mixtures thereof, especially the tertiary peroxides further containing primary peroxides, in the presence of a solvent, especially a lower alcohol solvent, using a palladium catalyst and a hydrogen gas.

The improved process can remove the conventional technical defect that the catalyst activity is reduced within a relatively short period of time and the ratio of palladium recovered from the spent catalyst is low. Furthermore, according to this process, aromatic alcohols can be produced advantageously on a commercial scale at high selectivities and yields with a prolonged catalyst life.

More specifically, this invention relates, in a process for producing an aromatic alcohol by catalytic hydrogenation of at least one tertiary peroxide selected from the group consisting of tertiary aromatic hydroperoxides and tertiary aromatic peroxides in the presence of a palladium catalyst in a lower aliphatic alcohol solvent to form the corresponding alcohol, to the improvement wherein said catalyst has a palladium metal surface area, determined by the CO chemisorption method, of up to about 200 $m^2/g \cdot Pd$.

Some suggestions have been made in the past about the catalytic hydrogenation of peroxides with hydrogen gas in the presence of a palladium catalyst to form alcohols corresponding to the peroxides.

For example, British Pat. No. 792,558 (published Mar. 26, 1958) discloses a process for producing organic peroxides which comprises reacting aromatic hydroperoxides with aliphatic or aromatic carbinols in an aliphatic carboxylic acid solvent using perchloric acid as a condensation catalyst. This Patent states that in order to produce the carbinols, the aromatic hydroperoxides are hydrogenated in the presence of a palladium catalyst supported on alumina.

Japanese Patent Publication No. 26961/64 (published Nov. 26, 1964) discloses a process for producing α-cumyl alcohol which comprises catalytically hydrogenating cumene hydroperoxide or dicumyl peroxide which falls into the category of tertiary aromatic hydroperoxides or aromatic peroxides in the presence of a hydrogenation catalyst such as platinum, palladium or Raney nickel in a saturated hydrocarbon or an aromatic hydrocarbon having saturated side chains as a solvent at a temperature of $-20°$ to $80°$ C.

Japanese Laid-Open Patent Publication No. 4036/75 (laid open on Jan. 16, 1975) discloses a process for producing α-cumyl alcohol which comprises catalytically hydrogenating cumene hydroperoxide, a tertiary aromatic hydroperoxide, in the presence of a hydrogenation catalyst such as platinum, palladium or Raney nickel in a solvent such as hydrocarbons, alcohols or ketones.

In all of these prior techniques, the activity of the palladium catalyst undergoes the trouble of degradation within relatively short periods of time. These prior patent documents do not at all touch upon this trouble, and naturally, give no information or suggestion which would be conducive to the elimination of such a trouble.

The present inventors made investigations in order to eliminate such a trouble of the prior art, and found that good results can be produced by selecting lower aliphatic alcohol solvents, but this alone does not lead to the satisfactory solution of the aforesaid technical problem. On further investigation, the present inventors found that the palladium metal surface area of the palladium catalyst constitutes an important factor for the maintenance of its catalytic activity.

Further investigations based on the aforesaid new findings have finally led to the discovery that by using a palladium catalyst having a lower palladium metal surface area than those of palladium catalysts heretofore used for hydrogenation, especially a palladium catalyst having a palladium metal surface area, determined by the CO chemisotrption method, of up to about 200 $m^2/g$ of Pd, the deterioration of the catalyst activity can be markedly prevented, the reduction in the ratio of palladium recovered can be avoided, and aromatic alcohols can be produced commercially advantageously from tertiary peroxides in high selectivities and yields with an increased catalyst life.

It is an object of this invention therefore to provide an improved process for producing aromatic alcohols from tertiary organic hydroperoxides and/or tertiary organic peroxides.

The above and other objects and advantages of this invention will become more apparent from the following description.

The tertiary peroxide used in this invention is at least one tertiary aromatic hydroperoxide and/or at least one tertiary aromatic peroxide, which may further include at least one primary aromatic hydroperoxide and/or at least one primary aromatic peroxide.

Examples of the tertiary aromatic hydroxyperoxides are those of the following formulae.

In the above formulae (1) and (2), $R_1$ and $R_4$ each represent an aromatic hydrocarbon group optionally having a substituent, and each of $R_2$, $R_3$, $R_5$, $R_6$, $R_7$ and $R_8$ represents an optionally substituted aliphatic, alicyclic or aromatic hydrocarbon group. Examples of the substituents are alkyl groups having 1 to 4 carbon atoms such as methyl, ethyl, isopropyl, n-propyl, n-butyl, sec-butyl and isobutyl. Examples of the aromatic hydrocarbon group are aromatic hydrocarbon groups having 6 to 16 carbon atoms and being optionally substituted, such as phenyl, methylphenyl, dimethylphenyl, isopropylphenyl, diisopropyl phenyl, naphthyl, methylnaphthyl, dimethylnaphthyl, isopropylnaphthyl and diisopropylnaphthyl. Examples of the aliphatic hydrocarbon groups are those having 1 to 4 carbon atoms and optionally having the substituents exemplified hereinabove. Specific examples are methyl, ethyl, isopropyl, n-propyl, n-butyl, sec-butyl, and isobutyl. The aliphatic hydrocarbon groups are, for example, those having 1 to 6 carbon atoms and optionally containing the substituents, such as cyclopropyl, cyclobutyl, cyclopentyl and cyclohexyl.

Examples of suitable tertiary aromatic hydroperoxides of formulae (1) and (2) include aromatic hydroperoxides having 9 to 16 carbon atoms, such as cumene hydroperoxide, tertiary cymene hydroperoxide, m- or p-diisopropylbenzene monohydroperoxide, 3,5-dimethylcumene hydroperoxide, m- or p-diisopropyl benzene dihydroperoxide, and isopropyl naphthalene hydroperoxide.

These tertiary aromatic hydroperoxides may, for example, include at least one primary aromatic hydroperoxide, and in this case, the improving effect of the process of this invention can be exhibited to a greater extent. Examples of such a mixture are autoxidation products of cymene or dimethylcumene which are well known per se. When cymene or dimethylcumene is autoxidized to produce the corresponding hydroperoxide, the product is a mixture of a primary hydroperoxide formed as a result of oxidation of the methyl group and a tertiary hydroperoxide formed as a result of oxidation of the isopropyl group. Especially good results can be achieved when the process of this invention is applied to such a mixture.

Examples of the tertiary aromatic peroxides are those of the following formulae.

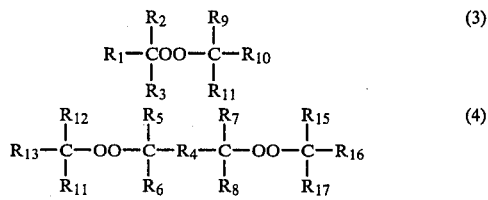

In formulae (3) and (4), $R_1$ through $R_8$ are the same as defined hereinabove, and $R_9$ to $R_{17}$ represent aliphatic, alicyclic or aromatic hydrocarbon groups optionally having the substituents exemplified hereinabove. Specific examples of the tertiary aromatic peroxides of formulae (3) and (4) include peroxides having 12 to 30 carbon atoms, such as bis($\alpha,\alpha$-dimethylbenzyl)peroxide, bis($\alpha$-methyl-$\alpha$-ethylbenzyl) peroxide, bis($\alpha,\alpha$-diethylbenzyl) peroxide, bis($\alpha,\alpha$-dimethylnaphthylmethyl) peroxide, bis($\alpha,\alpha$-dimethyl-p-isopropylbenzyl) peroxide, bis($\alpha,\alpha$-dimethyl-m-isopropylbenzyl) peroxide, $\alpha,\alpha$-dimethylbenzyl($\alpha,\alpha$-dimethyl-p-methylbenzyl) peroxide, and $\alpha,\alpha$-dimethyl-p-methylbenzyl-($\alpha,\alpha$-dimethyl-m-methylbenzyl) peroxide. When such a tertiary aromatic peroxide is used, too, greater effects can be achieved by applying the process of this invention to starting materials composed of the tertiary aromatic peroxides and primary aromatic peroxides, for example those of the aforesaid formulae in which any one combination of $R_2$-$R_3$, $R_9$-$R_{11}$, $R_5$-$R_6$, and $R_7$-$R_8$ is H-H.

In the process of this invention, the selection of a lower aliphatic alcohol solvent and the use of a palladium catalyst having a specified palladium metal surface area not suggested heretofore are essential in performing the catalytic hydrogenation of the tertiary peroxides.

The palladium catalyst used in this invention is required to have a palladium metal surface area, determined by the CO chemisorption method, of up to about 200 m²/g·Pd, for example about 10 to about 200 m²/g of Pd. The metal surface area of the palladium catalyst used in this invention is far smaller than those of conventional palladium catalysts.

If a palladium catalyst having a palladium metal surface area of more than about 200 m²/g of Pd, for example about 250 to 300 m²/g·Pd or more in most frequently utilized conventional palladium catalysts, is used, the maintenance of its activity is poor even if a lower alcohol is selected as a reaction solvent, as is clearly seen from a comparison of Example 7 with Comparative Example 2 in this application. As a result, the palladium metal supported on the carrier dissolves in the reaction mixture to degrade the catalyst, or the ratio of recovery of palladium is reduced inevitably. These phenomena occur especially when tertiary peroxides containing primary peroxides are catalytically hydrogenated. The mechanism of the occurrence of such phenomena has not yet been fully elucidated. It is theorized however that the primary hydroperoxide oxidizes part of the palladium metal to form a palladium ion, and the palladium ion dissolves in the reaction mixture. It should be understood in this regard that the scope of this invention is in no way limited by this theoretical consideration.

In the present invention, the palladium metal surface area of the palladium catalyst used in this invention is determined by the CO chemisorption method described in "Analytical Chemistry", Vol. 34, No. 13, December 1962, page 1829.

The flow adsorption apparatus shown in FIG. 1 accompanying this application is used in this method. This apparatus comprises a differential gear pump A, an oil reservoir B, an oil-mercury reservoir C, a 1-liter gas-mercury flask D, selector valves E, F and G with Teflon plugs, a 6-way gas sampling valve H, a temperature regulated conductivity cell J, a rotameter N, a 4-way valve K, a needle valve P, sample tubes L and a soap film flow meter M.

The procedure of this measuring method is as follows:

The catalyst sample is dried and weighed into the sample tube. The sample tube is connected to the system and hydrogen is passed over the sample at a rate of 50 cc per minute. After all the air is flushed out by hydrogen, the sample is placed in the furnace where it is reduced for 2 hours at 500° C. Hydrogen is then replaced by helium pumped at a constant rate of 10 cc per minute. The sample tube is allowed to cool to room temperature and placed in a water bath of 25° C. After temperature equilibration, the sample is ready for adsorption. An amount of CO, corresponding to approximately twice the volume of CO expected to be adsorbed, is then injected into the helium stream. The slug of carbon monoxide passes first through the reference side of the conductivity cell, then through the catalyst bed, and finally through the sample side of the conductivity cell. Two peaks, whose areas correspond to the amount of CO present before and after adsorption, are recorded and integrated. The difference in peak areas serves directly as a measure of CO adsorption on the sample.

Palladium catalyst having a palladium metal surface area in the specified range can be prepared by various means. For example, a Pd-Al₂O₃ catalyst in general use can be prepared by exchanging the surface portion of alumina powder with palladium ammine complex cations [Pd(NH₃)$_m$²⁺], washing the product with deionized pure water, and calcining it for 2 hours in the air and for another 2 hours in a stream of hydrogen. The Pd metal surface area of this catalyst can be regulated by properly selecting the calcination temperature in the air and the reducing temperature in hydrogen and thus changing the degree of sintering of palladium metal.

In the process of this invention, palladium is preferably supported on a carrier. Examples of the carrier are alumina, diatomaceous earth, activated charcoal, zeolite, calcium carbonate, silica, silica-alumina, barium sulfate, and titanium oxide. The use of alumina is preferred.

Preferably, the palladium catalyst has a high activity at low temperatures because the hydroperoxides and peroxides to be hydrogenated have poor heat stability. Furthermore, since it is used repeatedly, it should desirably be easy to separate from the reaction mixture and have high mechanical strength. In view of this, the alumina-supported palladium catalyst is especially preferred.

In particular, the use of an alumina carrier having an average particle diameter of 5 to 200 microns, preferably 20 to 100 microns, and a bulk density of 0.2 to 0.7 g/ml, preferably 0.3 to 0.6 g/ml is preferred because the resulting supported catalyst is easy to separate from the reaction mixture and has high activity. The suitable amount of palladium to be supported on the carrier, especially alumina, is about 0.1 to about 10% by weight.

Excepting the use of the palladium catalyst having the specified palladium metal surface area and a lower aliphatic alcohol as a reaction solvent, the catalytic hydrogenation in the process of this invention can be performed by means and procedures known per se.

Examples of the lower aliphatic alcohol solvent are methanol, ethanol, n-propanol, and isopropanol. The lower aliphatic alcohol may contain not more than 50% by weight of another solvent such as hydrocarbons, ethers, ketones and other alcohols.

The amount of the reaction solvent used is, for example, about 0.1 to about 20 parts by volume per part by volume of the starting hydroperoxide and/or peroxide. The amount of the palladium catalyst used is, for example, about 0.01 to about 10 g, preferably about 0.1 to about 1 g, per liter of the starting material and the reaction solvent combined.

The reaction temperature is generally about 0° to about 150° C., preferably about 20° to about 100° C. The hydrogen pressure is maintained generally at about 1 to about 50 kg/cm$^2$ (absolute), preferably 1 to 10 kg/cm$^2$ (absolute).

The catalytic hydrogenation can be performed, for example, by a procedure which comprises dissolving the starting hydroperoxide and/or peroxide in the lower aliphatic alcohol solvent, and while suspending the palladium catalyst in the solution, introducing hydrogen into a hydrogenation reaction zone containing the aforesaid materials. The reaction can be performed either batchwise, semi-continuously or continuously. Preferably, the conversion of the starting hydroperoxide and/or peroxide in this reaction is maintained at more than about 95% especially more than about 99%, because at such conversions, it is possible to reduce the amount of dissolved palladium to a greater degree and maintain a high activity of the catalyst for a longer period of time.

After the reaction is completed, the catalyst may be separated for reuse by, for example, allowing the reaction mixture to stand. The desired aromatic alcohol can be separated from the liquid phase by distillation or other separating means.

According to this invention, the reduction of the catalyst activity is small and the catalyst can be regenerated and repeatedly used even when the starting material contains a primary aromatic hydroperoxide or peroxide.

The following Examples illustrate the present invention in greater detail.

EXAMPLES 1 to 6 and COMPARATIVE EXAMPLE 1

One gram of Al$_2$O$_3$ powder having about 2% of Pd supported thereon, as shown in Table 1, was placed in a 200 ml continuous hydrogenating reactor equipped with a reflux condenser at an exhaust gas outlet, a stainless steel filter (2μ) at a reaction mixture outlet, a hydrogen introducing tube and a stirrer. While maintaining the temperature of the inside of the reactor at 60° C., a methanol solution containing 3.38% by weight of primary cymene hydroperoxide (CyHP) and 23.62% by weight of tertiary CyHP and 10 moles, per mole of CyHP, of hydrogen gas were continuously fed into the reactor. While suspending the catalyst, the starting materials were continuously hydrogenated at atmospheric pressure. The residence time in the reactor was 30 minutes, and the stirrer was operated at 750 rpm.

The catalyst which was trapped by the filter at the reaction mixture outlet was back-washed intermittently with the reaction mixture, and returned to the reactor. The amount of Pd dissolved in the reaction mixture was measured by emission spectroanalysis.

Table 1 shows the Pd surface areas of the Pd-Al$_2$O$_3$ catalysts used, and the amount of Pd dissolved and the percent dissolution of Pd determined after a run of 8 hours.

TABLE 1

| Items | Comparative Example 1 | Example 1 | 2 | 3 | 4 | 5 | 6 |
|---|---|---|---|---|---|---|---|
| Crystal form of Al$_2$O$_3$ | γ | γ | γ | γ | α | α | α |
| Average particle diameter (μ) | 48 | 49 | 47 | 46 | 34 | 34 | 37 |
| Bulk density (g/ml) | 0.39 | 0.41 | 0.40 | 0.39 | 0.61 | 0.59 | 0.63 |
| Amount of Pd supported (% by weight) | 1.92 | 1.91 | 2.00 | 2.00 | 2.60 | 2.10 | 2.11 |
| Pd surface area (m$^2$/g · Pd) | 255 | 188 | 77 | 17 | 178 | 110 | 65 |
| Amount of catalyst charged (g) | 1.00 | 1.00 | 1.00 | 1.00 | 1.00 | 1.00 | 1.00 |
| Amount of Pd charged (mg) | 19.2 | 19.1 | 20.0 | 20.0 | 26.0 | 21.0 | 21.1 |
| Amount of Pd dissolved (mg) | 10.2 | 6.5 | 3.2 | 3.5 | 4.2 | 3.7 | 3.0 |
| Percent dissolution of Pd (%) | 53 | 34 | 16 | 17 | 16 | 14 | 14 |
| Conversion of tertiary CyHP (mole %) | 45 | 46 | 47 | 44 | 46 | 44 | 45 |
| Selectivity for dimethyltolyl carbinol (mole %) | 99 | 100 | 100 | 100 | 100 | 100 | 100 |
| Conversion of primary CyHP (mole %) | 48 | 56 | 56 | 48 | 56 | 48 | 48 |
| Selectivity for isopropylbenzyl alcohol | | | | | | | |

TABLE 1-continued

| Items | Comparative Example 1 | Example 1 | Example 2 | Example 3 | Example 4 | Example 5 | Example 6 |
|---|---|---|---|---|---|---|---|
| (mole %) | 50 | 71 | 71 | 67 | 86 | 83 | 83 |

*The percent dissolution of Pd is the percentage of the Pd (g) dissolved in the reaction mixture based on the Pd (g) charged.

EXAMPLE 7

Using the same apparatus and procedure as used in Examples 1 to 6, a methanol solution containing 3.9% by weight of primary CyHP and 26.1% by weight of tertiary CyHP was subjected continuously to hydrogenation for 350 hours. The reaction conditions were as follows:

Reaction temperature: 60° C.
Residence time: 75 minutes
Concentration of 2% Pd-$Al_2O_3$ catalyst: 1.5% (w/v)
Operating speed of the stirrer: 750 rpm
Mole ratio of $H_2$/CyHP fed: 10

The catalyst used was a Pd-$Al_2O_3$ powder having a Pd surface area of 77 $m^2$/g·Pd, an average particle diameter of 47 microns and a Pd content of 2.0%.

During the period of 350 hours, almost all CyHP was reduced to the corresponding alcohol, and no decrease in catalytic activity was noted.

From the catalyst used for 350 hours, 91% of Pd (based on Pd charged) was recovered. In other words, the amount of Pd dissolved in the reaction mixture was only 9%. The other results were as follows:

Conversion of tertiary CyHP: 100 mole%
Conversion of primary CyHP: 100 mole%
Selectivity for dimethyltolyl carbinol: 100 mole%.
Selectivity for isopropylbenzyl alcohol: 91 mole%

COMPARATIVE EXAMPLE 2

Example 7 was repeated except that the catalyst was changed to a Pd-$Al_2O_3$ powder having a Pd surface area of 255 $m^2$/g·Pd, an average particle diameter of 57 microns and a Pd content of 1.92%.

In one hour after the starting of the reaction, the conversion of CyHP was 100%. But it decreased with time, and at the end of 70 hours, decreased to 10%. Only 8% (based on the charged Pd) of Pd was recovered from the used catalyst, and most of the Pd dissolved in the reaction mixture.

The selectivity for dimethyltolyl carbinol from tertiary CyHP was 100%.

EXAMPLES 8 to 10

Using the same apparatus and procedure as in Examples 1 to 6, 2 g (1 W/V %) of a Pd-$Al_2O_3$ powder having a Pd surface area of 165 $m^2$/g·Pd and a Pd content of 2.0% was added, and a methanol solution containing 3.38% by weight of primary CyHP and 23.62% by weight of tertiary CyHP was subjected to continuous hydrogenation with a residence time of 20, 30 and 60 minutes, respectively. The other reaction conditions were as follows:

Reaction temperature: 60° C.
Mole ratio of $H_2$/CyHP fed: 10
Operating speed of the stirrer: 750 rpm The total reaction periods were adjusted to 9, 4.5, and 3 hours, respectively, corresponding to the residence time of 20, 30 and 60 minutes. The feed amount of the starting solution was made constant in each run, and the amount of Pd dissolved was measured.

The results are shown in Table 2.

TABLE 2

| Example | 8 | 9 | 10 |
|---|---|---|---|
| Residence time (minutes) | 20 | 30 | 60 |
| Percent dissolution of Pd (%) | 11 | 6 | 1 |
| Conversion of tertiary CyHP (mole %) | 58 | 79 | 100 |
| Selectivity for dimethyltolyl carbinol (mole %) | 100 | 100 | 100 |
| Conversion of primary CyHP (mole %) | 64 | 88 | 100 |
| Selectivity for isopropylbenzyl alcohol (mole %) | 88 | 91 | 88 |

COMPARATIVE EXAMPLE 3 and EXAMPLE 11

One gram of $Al_2O_3$ powder having about 2% of Pd supported thereon was placed in a 200 ml continuous hydrogenating reactor equipped with a reflux condenser at an exhaust gas outlet, a stainless steel filter (2μ) at a reaction mixture outlet, a hydrogen-introducing tube and a stirrer. While maintaining the temperature of the inside of the reactor at 60° C., a methanol solution of cumene hydroperoxide (CHP) in a concentration of 25% by weight and 15 moles, per mole of the CHP, of hydrogen gas were continuously fed into the reactor, and hydrogenation was continuously performed at atmospheric pressure while suspending the catalyst.

The catalyst trapped in the filter at the reaction mixture outlet was back-washed intermittently with the reaction mixture, and returned to the reactor. By this back-washing operation, the concentration of the catalyst in the reactor was maintained always constant. The amount of Pd dissolved in the reaction mixture was measured by emission spectroanalysis.

The residence time was 45 minutes, and the stirrer was operated at 750 rpm.

Table 3 shows the amount of Pd dissolved and percent dissolution of Pd after a feeding time of 8 hours, and the results obtained.

TABLE 3

| Item | Comparative Example 3 | Example 11 |
|---|---|---|
| Crystal form of $Al_2O_3$ | | |
| Average particle diameter (μ) | 38 | 36 |
| Bulk density (g/ml) | 0.60 | 0.62 |
| Amount of Pd supported (wt. %) | 1.93 | 2.22 |
| Pd surface area ($m^2$/Pd · g) | 253 | 174 |
| Amount of the catalyst charged (g) | 4.00 | 1.00 |
| Amount of Pd charged (mg) | 77.2 | 22.2 |
| Amount of Pd dissolved (mg) | 9.8 | 0.9 |
| Percent dissolution of Pd (%) | 12.7 | 4.1 |
| Conversion of CHP (mole %) | 94 | 99 |
| Selectivity for α-cumyl alcohol (mole %) | 99 | 100 |

EXAMPLES 12 to 15

Example 11 was repeated except that a methanol solution of each of dicumylperoxide (DCP), p-diisopropylbenzene monohydroperoxide (p-MHP), p-diisopropylbenzene dihydroperoxide (p-DHP) and m-diisopropylbenzene dihydroperoxide (m-DHP) in each of the concentrations shown in Table 4 was used as the starting material, the residence time was changed to 60 minutes, and the $H_2$/peroxide feed ratio was maintained at 15.

The results are shown in Table 4.

TABLE 4

| | Example | | | |
|---|---|---|---|---|
| | 12 | 13 | 14 | 15 |
| | 15 wt. % | 30 wt. % | 15 wt. % | 15 wt. % |
| Item | DCP | p-MMP | p-DHP | m-DHP |
| Conversion of hydroperoxide (mole %) | 100 | 100 | 100 | 100 |
| Selectivity for carbinol (mole %) | 98 | 100 | 99* | 99* |
| Pd dissolved (mg) | 0.8 | 0.8 | 0.7 | 0.9 |
| Percent dissolution of Pd (%) | 2.7 | 3.6 | 3.2 | 4.1 |

*Dicarbinol

EXAMPLE 16

Example 11 was repeated except that a methanol solution of a mixture of CHP and DCP was used as the starting material, the residence time was changed to 60 minutes, and the $H_2$/(CHP+DCP) feed mole ratio was maintained at 15.

The results were as follows:
Conversion of CHP: 100 mole%
Conversion of DCP: 95 mole%
Selectivity for α-cumyl alcohol: 100%
Amount of Pd dissolved (after a feeding time of 8 hours): 0.5 mg
Percent dissolution of Pd (after a feeding time of 8 hours): 2.2%

What we claim is:

1. In a process for producing an aromatic alcohol by catalytic hydrogenation of at least one tertiary peroxide selected from the group consisting of tertiary aromatic hydroperoxides having 9 to 16 carbon atoms in which the aromatic ring is selected from the group consisting of naphthyl, phenyl and benzyl and tertiary aromatic peroxides having 12 to 30 carbon atoms in which the aromatic ring is selected from the group consisting of naphthyl, phenyl and benzyl in the presence of hydrogen gas and a palladium catalyst supported on a carrier in a lower aliphatic alcohol solvent to form the corresponding alcohol; the improvement wherein said catalyst has a palladium metal surface area, determined by the CO chemisorption method, of from about 10 to about 200 $m^2/g$. Pd and is supported on an alumina or a silica-alumina carrier.

2. The process of claim 1 wherein said tertiary peroxide further comprises at least one primary peroxide selected from the group consisting of primary aromatic hydroperoxides and primary aromatic peroxides.

3. The process of claim 1 wherein said catalytic hydrogenation is carried out until the conversion of said tertiary peroxide reaches at least about 95%.

* * * * *

UNITED STATES PATENT AND TRADEMARK OFFICE
CERTIFICATE OF CORRECTION

PATENT NO. : 4,322,567
DATED : March 30, 1982
INVENTOR(S) : Fujihisa MATSUNAGA, Norio OHNO and Hirohiko NAMBU It is certified that error appears in the above—identified patent and that said Letters Patent is hereby corrected as shown below:

On the title page,

[30] Foreign Application Priority Data should read;

-- June 18, 1979 [JP] Japan........54-75624 --.

*Signed and Sealed this*

*Eighteenth* Day of *May 1982*

[SEAL]

*Attest:*

*Attesting Officer*

GERALD J. MOSSINGHOFF
*Commissioner of Patents and Trademarks*